United States Patent
Correns et al.

(10) Patent No.: US 10,436,712 B2
(45) Date of Patent: Oct. 8, 2019

(54) DEVICES AND METHODS FOR SPECTROSCOPIC ANALYSIS

(71) Applicant: Carl Zeiss Microscopy GmbH, Jena (DE)

(72) Inventors: Nico Correns, Weimar (DE); Michael Rode, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 15/909,008

(22) Filed: Mar. 1, 2018

(65) Prior Publication Data

US 2018/0188175 A1    Jul. 5, 2018

Related U.S. Application Data

(62) Division of application No. 14/276,101, filed on May 13, 2014, now Pat. No. 9,927,361.

(30) Foreign Application Priority Data

May 16, 2013  (DE) ......................... 10 2013 209 104

(51) Int. Cl.
*G01N 21/64* (2006.01)
*G01J 3/28* (2006.01)
(Continued)

(52) U.S. Cl.
CPC ............. *G01N 21/64* (2013.01); *G01J 3/28* (2013.01); *G01N 23/2254* (2013.01); *G01N 2021/213* (2013.01); *G01N 2223/501* (2013.01)

(58) Field of Classification Search
CPC ............. G01N 21/64; G01N 21/6458; G01N 15/1434; G01N 15/1459;
(Continued)

(56) References Cited

U.S. PATENT DOCUMENTS 3,514,599 A    5/1970   Campbell
3,523,734 A *  8/1970   Brehm ..................... G01J 3/18
                                                      356/331
(Continued)

FOREIGN PATENT DOCUMENTS

AT       21 577 E      12/1986
DE       2029141 A     12/1970
(Continued)

OTHER PUBLICATIONS

German Office Action, with translation thereof, for corresponding DE Appln No. 10 2013 209 104.4, dated Apr. 16, 2014.
(Continued)

*Primary Examiner* — Taeho Jo
(74) *Attorney, Agent, or Firm* — Fish & Richardson P.C.

(57) ABSTRACT

The present invention relates to devices and methods for spectrometric analysis of light-emitting samples. The device comprises a particle beam source, which generates a primary particle beam directed to the sample in such a way that the primary particle beam is incident on the sample and photons are released from the sample due to the interaction between primary particle beam and sample material. Moreover, the device comprises a plurality of light-pickup elements, which are suitable for capturing the photons released from the sample, wherein the light-pickup elements capture the photons emitted in the respectively assigned solid-angle range. Furthermore, the device comprises conduction elements, which are embodied to forward captured photons to an evaluation unit, and an analysis system, which comprises a plurality of evaluation units in such a way that photons captured by each light-pickup element are analyzed spectrally.

20 Claims, 8 Drawing Sheets

(51) Int. Cl.
*G01N 23/2254* (2018.01)
*G01N 21/21* (2006.01)

(58) Field of Classification Search
CPC ..... G01N 2015/0038; G01N 2021/213; G01N 21/774; G01N 2021/633; G01N 2223/501; G01N 23/2254; G01J 3/28
USPC ...................................................... 250/459.1
See application file for complete search history.

(56) References Cited

U.S. PATENT DOCUMENTS

| | | | |
|---|---|---|---|
| 3,567,928 | A | 3/1971 | Davies et al. |
| 3,907,403 | A | 9/1975 | Meada |
| 4,141,623 | A | 2/1979 | Dubost |
| 4,645,344 | A | 2/1987 | Thevenon |
| 4,650,321 | A | 3/1987 | Thompson |
| 4,988,872 | A | 1/1991 | Nagatsuka et al. |
| 5,045,695 | A | 9/1991 | Rule |
| 5,281,820 | A | 1/1994 | Groh et al. |
| 5,963,320 | A * | 10/1999 | Brooks ............... G01J 3/06 356/310 |
| 6,081,325 | A | 6/2000 | Leslie |
| 6,226,085 | B1 * | 5/2001 | Weber ............... G01B 11/303 356/236 |
| 6,310,352 | B1 | 10/2001 | Gross et al. |
| 6,599,253 | B1 | 7/2003 | Baum |
| 6,614,528 | B1 | 9/2003 | Bohle |
| 6,768,123 | B2 | 7/2004 | Giering |
| 6,839,135 | B2 | 1/2005 | Hamm et al. |
| 7,317,515 | B2 | 1/2008 | Buijsse et al. |
| 8,294,097 | B2 | 10/2012 | Katane et al. |
| 8,513,604 | B2 | 8/2013 | Thomas et al. |
| 8,749,538 | B2 | 6/2014 | Webster |
| 10,006,811 | B2 * | 6/2018 | Dholakia ............... G01J 3/0205 |
| 2006/0060782 | A1 | 3/2006 | Khursheed |
| 2006/0268270 | A1 * | 11/2006 | Kerstan ............... G01J 3/02 356/328 |
| 2007/0188765 | A1 * | 8/2007 | Zhao ............... G01J 3/02 356/479 |
| 2007/0201039 | A1 * | 8/2007 | Grygier ............... G03H 1/22 356/521 |
| 2008/0266549 | A1 | 10/2008 | Schiedemeyer |
| 2009/0109428 | A1 * | 4/2009 | Ohkubo ............... G01J 1/04 356/236 |
| 2009/0225314 | A1 * | 9/2009 | Warren ............... G01J 3/02 356/328 |
| 2010/0014076 | A1 | 1/2010 | Henneberg et al. |
| 2010/0220311 | A1 | 9/2010 | Hall |
| 2011/0003093 | A1 | 1/2011 | Hayashi |
| 2011/0007311 | A1 | 1/2011 | Correns |
| 2011/0155926 | A1 * | 6/2011 | Ohkubo ............... G01J 3/0254 250/459.1 |
| 2011/0220793 | A1 | 9/2011 | Thomas et al. |
| 2013/0068966 | A1 | 3/2013 | Kociak et al. |
| 2013/0075604 | A1 | 3/2013 | Bean |
| 2013/0252340 | A1 | 9/2013 | Haertling et al. |
| 2014/0027632 | A1 * | 1/2014 | Stowe ............... G01N 23/2254 250/306 |
| 2014/0233029 | A1 * | 8/2014 | Dobschal ............... G01J 3/0205 356/328 |
| 2014/0339438 | A1 | 11/2014 | Correns |

FOREIGN PATENT DOCUMENTS

| | | |
|---|---|---|
| DE | 2037178 A1 | 2/1971 |
| DE | 22 45 696 A | 3/1973 |
| DE | 239100 A1 | 9/1986 |
| DE | 38 41 136 A1 | 6/1990 |
| DE | 44 08 057 A1 | 9/1995 |
| DE | 195 23 140 A1 | 1/1997 |
| DE | 196 10538 A1 | 9/1997 |
| DE | 19731226 | 8/1998 |
| DE | 198 53 754 B4 | 5/2000 |
| DE | 200 06 642 U1 | 8/2000 |
| DE | 10056770 A1 | 5/2002 |
| DE | 101 23443 A1 | 11/2002 |
| DE | 101 27836 A1 | 1/2003 |
| DE | 203 07 617 U1 | 8/2003 |
| DE | 10 2007 027 284 A1 | 12/2008 |
| DE | 10 2008 012 635 A1 | 9/2009 |
| DE | 10 2008 052 357 A1 | 10/2009 |
| DE | 102009015341 A1 | 10/2010 |
| DE | 102009046211 | 5/2011 |
| DE | 102010005723 A1 | 7/2011 |
| DE | 20 2010 000 233 U1 | 9/2011 |
| DE | 10 2010 053 723 A1 | 5/2012 |
| DE | 10 2011 082 468 B4 | 3/2013 |
| DE | 10 2011 082 469 B4 | 3/2013 |
| DE | 11 2010000743 T5 | 8/2013 |
| EP | 1726930 A1 | 11/2006 |
| EP | 1 655 597 B1 | 1/2008 |
| EP | 1 953537 A1 | 8/2008 |
| FR | 1568134 A1 | 5/1969 |
| FR | 2634889 A1 | 2/1990 |
| GB | 2 453 860 | 4/2009 |
| WO | WO 95/24638 | 9/1995 |
| WO | WO 02/40973 | 5/2002 |
| WO | WO 2011/148073 A1 | 12/2011 |
| WO | WO 2012/008836 A | 1/2012 |
| WO | WO 2012/097770 A1 | 7/2012 |

OTHER PUBLICATIONS

Marini, F. et al.: "Artificial Neural Networks in Chemometrics: History, Examples and Perspectives, Multivariate Analysis and Chemometrics applied to Environmental and Cultural Heritage", Nemi (RM), Oct. 2-4, 2006, Italy.
C.M. Macrae et al., "Quantitative Cathodoluminescence Mapping with Application to a Kalgoorlie Scheelite," Microsc. Microanal. 15, 222-230, 2009.
German Office Action, with translation thereof, for DE Appl No. 10 2013 209 104.4, dated Dec. 3, 2015.
European Office Action, with translation thereof, for EP Appl No. 14 168 505.7-1559, dated Mar. 10, 2016.
European Search Report for corresponding Appl No. 14 168 505.7, dated Jan. 17, 2017.
Naes T. et al., "A User-Friendly Guide to Multivariate Calibration and Classification", NIR Publications, Chichester, UK (2002), Chapters 5-8, pp. 27-91.
European Search Report, with translation thereof, for corresponding Appl No. 18176182.6, dated Sep. 25, 2018.
De Mets M, "Improved cathodoluminescence detection system," J of Physics E; Scientific Instruments, vol. 7, No. 12, Dec. 1974, pp. 971-972.

* cited by examiner

DEVICES AND METHODS FOR SPECTROSCOPIC ANALYSIS

CROSS-REFERENCE TO RELATED APPLICATIONS

This application is a divisional of, and claims priority under 35 USC 120 to, U.S. application Ser. No. 14/276,101, filed Mar. 13, 2014, which claims benefit under 35 U.S.C. § 119 to German Application No. 10 2013 209 104.4, filed May 16, 2013, the entire contents of which are incorporated by reference herein.

The invention relates to methods and devices for spectrometric analysis of luminescent samples.

Luminescence is understood to mean the emission of light, i.e. electromagnetic radiation with wavelengths in the visible or adjacent wavelength range (infrared and ultraviolet). In order to be able to observe luminescence, a material having luminescent properties is excited by excitation processes to emit light. By way of example, the excitation can be brought about by irradiation with photons or electrons. This is referred to as photoluminescence in the case of excitation by photons, e.g. via UV light. Luminescence is referred to as cathodoluminescence (CL) if the light emission was excited by the incidence of electrodes which were previously emitted by a cathode and accelerated in an electric field. The duration of the light emission can be very different and range between a few milliseconds and a number of hours: quickly decaying luminescence appearances are referred to as fluorescence and long-term light emission is referred to as phosphorescence.

The generation of luminescence phenomena in semiconductors and inorganic crystals can be explained by the energy band model from semiconductor physics. In accordance with this model, the energy states in which the electrons can be situated are combined to form bands, wherein a distinction is made between a valence band and a conduction band. If primary particles, that is to say e.g. photons or electrons, are incident on the sample material, energy can be transferred from an incident primary particle to an electron of the sample material. If the energy is transferred to a valence electron, this electron can be lifted into an energy state assigned to the conduction band. However, in the case of fluorescence, the conduction electron immediately recombines with an electron hole in the valence band, i.e. returns to the energy level of the valence band. In the process, energy is released, which is emitted in the form of light quanta, the energy of which corresponds to the transition energy. In addition to such a direct band/band transition, indirect band transitions may also occur, in which part of the released energy is emitted in the form of heat (non-radiating recombination of the charge carriers).

In the case of organic molecules, the generation of luminescence can also be explained by virtue of electrons, which were previously lifted by excitation processes from an energetic ground state into an excited state, returning to the ground state and emitting light in the process.

The emitted luminescence light can be detected and used to generate images of the sample or to analyze the material properties of the sample. Thus, conclusions can be drawn about the properties of the luminescent material, preferably on the basis of intensity, spectral composition and time-dependent change in the intensity of the luminescence light. By way of example, this allows recombination centers to be determined, or lattice defects, impurities, phase formations or inhomogeneities in the dopant distribution to be identified. Typical examples of samples in which luminescence phenomena can be examined are semiconductor components, ceramics (e.g. technical catalysts), inorganic crystals and biomedical samples (e.g. tissue samples). It is also possible to examine organic compounds, for example in order to be able to identify chemical defects in the polymer structure of plastics, since undesired breaks in the polymer chains may, at a later stage, emanate from such defects.

However, integrated detection of the luminescence light, i.e. the detection of a summed signal, only supplies qualitative results since the cause for a change in the summed signal may lie in the simultaneous change of a plurality of parameters. It is therefore more advantageous to detect the luminescence light in an angle-resolved, spatially resolved and time-resolved manner and, in the process, register the respective wavelength spectrum of the released photons. The spectral analysis allows the electron transition responsible for the light emission to be identified since there is a direct relationship between transition energy and wavelength of the emitted photons from the wave equation and Planck's constant.

Since light is emitted in all directions, the largest possible solid angle over the sample should be registered so that as many photons emerging from the sample material as possible are detected. The angle-resolved detection allows conclusions to be drawn about material properties and texture of the sample, since the assumption can be made that photons originating from different depths of the structured sample are emitted in different solid angles. The time-resolved detection renders it possible to register the kinetics of the charge carrier recombinations, that is to say e.g. lifespan, reaction times, scattering mechanisms or capturing times. Moreover, it is advantageous to achieve a high spatial resolution. By way of example, this is possible in cathodoluminescence, since the incident electron beam can be focused on the sample surface, and so it is usually possible to achieve a spatial resolution of less than one micrometer.

In order to examine the spectral composition, use is generally made of spectrometers which typically comprise an entry slit (entry aperture), a dispersion element and a detector. A prism or a grating can serve as dispersion element. If the light to be analyzed passes the dispersion element, the spectral components of the light are deflected in different spatial directions: a spectrum is generated, which can be imaged via the detector and/or stored and processed for analysis purposes. Alternatively, use can also be made of filter-based spectrometers.

When the light beam passes through a diffraction grating, intensity maxima of the zero order of diffraction and of higher orders of diffraction are generated. The zero-order maximum is to be understood to mean the portion of the light which passes the diffraction grating without being spectrally divided. However, in conventional spectrometers, the zero order is not evaluated but rather suppressed by light traps in order to prevent interference of the spectrometric measurement.

Usually, spectrometers need to be continuously referenced during operation in order to compensate for changes in the surrounding influences—e.g. temperature variations—which would have a negative effect on the measurement. In order to carry out the referencing, it is conventional to interrupt the measurement at specific time intervals and to modify the measurement arrangement in such a way that a minimum value (dark reference) and a maximum value (bright reference) can be defined, between which all future measured values can then be arranged.

BRIEF DESCRIPTION OF THE RELATED PRIOR ART

DE 19731226 describes an imaging CL spectrometer for recording CL images and CL spectra in electro-optical instruments.

Furthermore, a combined device of light microscope and electron or ion microscope is known, which comprises a light-collecting device and a detector for detecting luminescence light.

Moreover, methods have been proposed in which the primary beam is emitted and directed to the sample and the luminescence light released from the sample material is captured.

Moreover, methods and devices for time-resolved spectroscopy via a PMD sensor are known, as is the use of compact miniaturized spectrometers.

The following documents can be considered to be the closest prior art:
WO2012/008836A
DE 102009046211
DE 19731226

OVERVIEW OVER THE INVENTION

It is an object of the present invention to propose devices and methods via which the wavelength spectrum of luminescence light can be detected. In the process, the detected photons are preferably registered in an angle-resolved manner. Alternatively, the detected photons are registered simultaneously in a spatially resolved and angle-resolved manner. Moreover, methods and devices are proposed, via which photons can be registered in a spatially resolved, angle-resolved and time-resolved manner.

According to the invention, this object is achieved by a device for spectrometric analysis of light-emitting samples, wherein the device comprises: a particle beam source which generates a primary particle beam directed to the sample so that the primary particle beam is incident on the sample and photons are released from the sample due to the interaction between primary particle beam and sample material; light-pickup elements suitable for capturing the photons released from the sample, wherein each light-pickup element captures photons emitted in a solid-angle range; conduction elements embodied to forward captured photons to an evaluation unit; and an analysis system comprising a plurality of evaluation units in such a way that photons captured by each light-pickup element are analyzed spectrally. The object is also achieved by a device for spectrometric analysis of light-emitting samples, wherein the device comprises: an imaging grating arranged so that photons released by the sample are dispersed; and a detector which detects the spectrum generated by dispersion. Advantageous configurations of the invention are specified by the disclosure. Moreover, the object is achieved by a method for spectroscopic analysis of samples, comprising the following steps: a) generating a primary particle beam directed to the sample in such a way that the primary particle beam is incident on the sample and photons are released from the sample due to the interaction between primary particle beam and sample material and released photons are able to move along a multiplicity of possible trajectories, wherein each one of the possible trajectories n is characterized by an elevation angle hn and an azimuth angle an and equivalent or similar trajectories are combined to solid-angle ranges of the trajectories; b) simultaneously capturing the released photons via a multiplicity of light-pickup elements, wherein each individual light-pickup element corresponds to a solid-angle range of the trajectories; c) forwarding the captured photons to an analysis system, wherein the analysis system comprises a multiplicity of evaluation units in such a way that an evaluation unit is assigned to each light-pickup element, and d) recording optical spectra in such a way that a spectrum is generated for each light-pickup element on the basis of the photons captured by this light-pickup element, and by advantageous configurations specified by the disclosure.

The particle-optical device according to the invention can be a scanning electron microscope (SEM), an ion microscope with focused ion beam (FIB), a light microscope or a combination instrument, which comprises two or more of the aforementioned particle-optical devices. It is also feasible to use a transmission electron microscope (TEM) as particle-optical device.

In an advantageous embodiment, the particle-optical device comprises at least one particle beam source. The particle beam source generates a primary particle beam of electrically charged particles, which is directed to the sample. The sample consists of at least one chemical substance with luminescence properties. The particles of the primary particle beam incident on the sample interact with the luminescence-capable sample material. As a result, interaction products in the form of photons are released from the sample. Since the focus of the primary particle beam is generally guided sequentially over the sample surface, the luminescence light is in each case only emitted on the impact point of the primary particle beam, and so the luminescence light can be detected in a spatially resolved manner.

In principle, each location on the sample can emit light, and so each location on the sample can be considered to be a punctiform light source. Proceeding from a light source, photons are potentially emitted in all directions, wherein the photons can follow a multiplicity of possible trajectories. In each case, these trajectories can be described by an elevation angle $h_n$ and an azimuth angle $a_n$. Since there are infinitely many possible trajectories, it is advantageous to group trajectories with a similar profile—that is to say trajectories that can be described by the same, approximately the same or similar solid angles—by virtue of defining that these trajectories belong to the same solid-angle range of the trajectories. The center points of the various solid-angle ranges in each case lie under different angles in relation to the incident primary particle beam, to be precise both in the direction of the elevation angle (vertical angle) and in the direction of the azimuth (horizontal angle).

Using a device in accordance with the present invention, it is possible to distinguish between photons moving in different solid-angle ranges and to detect these separately from one another. To this end, the device comprises a multiplicity of light-pickup elements, which are arranged over the sample surface in such a way that as many solid-angle ranges as possible can be registered and that each light-pickup element is assigned to a specific solid-angle range of the trajectories. The light-pickup elements are suitable for picking up and forwarding photons. It is advantageous if each light-pickup element is connected to a conduction element. However, it is also feasible for two or more light-pickup elements to be connected to one conduction element. The conduction elements are suitable for forwarding the photons picked up by a light-pickup element to an evaluation unit, via which the wavelength spectrum of the photons can be analyzed. Thus, this means that each evaluation unit is assigned to a solid-angle range of the trajectories via the direct assignment of light-pickup elements, conduction element and evaluation unit to one another. The evaluation units can be embodied as the channels of a multi-channel spectrometer. A multi-channel spectrometer—sometimes also referred to as a multi-beam spectrometer—is understood to mean a spectrometer which can record a plurality of complete spectra in parallel and, for example, is embodied in the form of a multi-channel Offner spectrometer. Offner-type spectrometers have been known for a relatively long time and typically comprise an entry slit, two concave mirrors and a diffraction grating, lying on a convex mirror, arranged between the mirrors. However, the invention is not restricted to an Offner spectrometer but can be carried out with any other multi-channeled spectrometer, wherein the signal readout can be simultaneous or in a time-offset manner. Alternatively, the evaluation units can be embodied as a multiplicity of miniaturized spectrometers such that a miniature spectrometer is assigned to each light-pickup element in this case.

Both embodiment alternatives render it possible to detect photons in an angle-resolved manner and to record the wavelength spectrum of the detected photons. For the spectral measurement, use can be made of spectrometers which, for example, record the wavelength range from UV to NIR (185 nm-2500 nm). Under vacuum conditions, it may be advantageous to work with wavelengths under 185 nm, for example 120 nm or less, or with wavelengths over 2500 nm, for example with 10 000 nm.

By the use of time-resolving photon detectors, it is moreover additionally possible to detect the spectra in a time-resolved manner.

Subsequently, the obtained wavelength spectra can be calculated by mathematical algorithms on the basis of chemical statistics (chemometrics) and analyzed and evaluated with the aid of available databases. The processes applied there are oriented to the demands of the respective application. A further advantageous embodiment comprises a first spectrometer which uses the radiation portion undergoing higher-order diffraction, that is to say e.g. first, second or third order. Moreover, this embodiment comprises a second spectrometer which uses the radiation portion of the zero-order diffraction. The radiation portion of the zero order usually remains unused in conventional spectrometric measurement designs, even though this radiation portion contains the whole spectrometric information and makes up approximately 50% of the irradiated energy. By using the zero diffraction order intensity maximum, the second spectrometer can be operated at the same time as the first spectrometer, without a performance loss occurring in the operation of the first spectrometer.

A further aspect of the invention comprises the simultaneous or timely referencing of the measured spectra. Here, the referencing preferably takes place within a time window that is smaller than the time window within which a change in the measurement design, which would require compensation, is expected. It is particularly advantageous if the spectroscopic measurement is not interrupted for referencing.

EXEMPLARY EMBODIMENTS

Exemplary embodiments of the invention will be explained below on the basis of figures. Here, components which correspond to one another in terms of the structure and function thereof are provided with reference signs that have the same numerals but are complemented with an additional letter to distinguish between these.

FIGS. 5a and 5b schematically show a further advantageous embodiment of the device according to the invention.

In FIGS. 2, 3 and 7, a sectional plane is depicted in an exemplary manner, wherein the view in a further sectional plane (not depicted here) perpendicular to the depicted sectional plane would be the same or similar.

Figure 1:
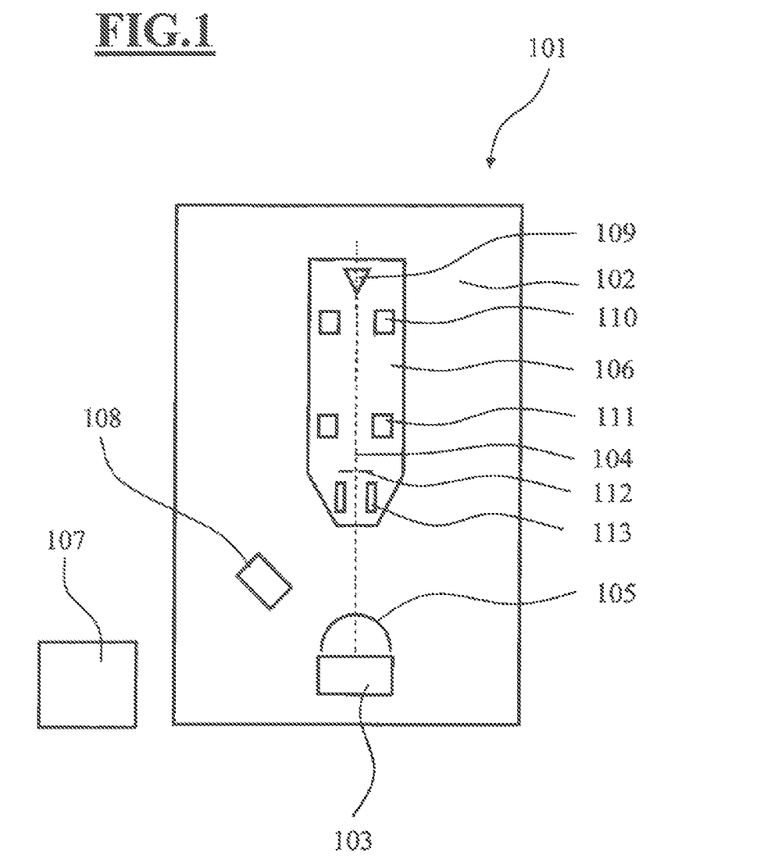
FIG. 1 shows a section through a model of a device according to the invention.

FIG. 1 schematically shows a special exemplary embodiment. FIG. 1 depicts a particle-optical device 101, which may be embodied as an electron beam instrument, for example as a scanning electron microscope. The particle-optical device 101 comprises a particle beam source 109, which is situated in a particle-optical column 106 and generates a primary particle beam 104, which is exposed to an acceleration voltage. The primary particle beam 104 is directed to the sample 103. The primary particle beam 104 is focused with the aid of lens-element systems 110, 111. After passing through an aperture stop 112, the focus of the particle beam is, via a deflection system 113, directed to the sample 103 to be examined and moved over the surface of the sample 103 line-by-line. The primary particle beam 104 can advantageously be modulated, for example by virtue of being able to be switched on and off or by virtue of the mean energy of the primary particles being able to be varied. The sample 103 consists of material with luminescent properties and is situated on a displaceable sample stage within a sample chamber 102, in which vacuum conditions are prevalent and which is embodied for holding a sample 103. The device 101 furthermore comprises a detection device 105, which is suitable to detect the photons released from the sample 103. The detected photons are forwarded to an analysis system 107 and evaluated there.

In particularly advantageous embodiments, the particle-optical device 101 moreover comprises at least one further detector 108, with the aid of which interaction products, which are generated by the interaction between primary particle beam 104 and sample material 103, can be detected. In addition to photons, other interaction products can also be generated, for example secondary electrons (SE) or back-scattered electrons (BSE). Usually, a BSE detector and/or an SE detector are used for detecting these interaction products, depending on whether back-scattered electrons (BSE) and/or secondary electrons (SE) are to be used for image generation. It is also conceivable to detect further interaction products using other suitable detectors, e.g. an x-ray detector.

The invention can also be carried out using a particle-optical device which is embodied as ion beam instrument or two-beam microscope. In principle, ion beam instruments and electron beam instruments have similar design. However—in contrast to electron beam instruments—ion beam instruments have an ion source as particle beam source instead of an electron source and only have electrostatic lens elements instead of magnetic lens elements or combined electrostatic/magnetic lens elements. Moreover, depending on the polarity of the ions, the polarities of the potentials and potential differences applied to the various components naturally also need to be adapted accordingly. A two-beam microscope is to be understood to mean a combination instrument made of an electron beam instrument and an ion beam instrument. A two-beam microscope comprises two particle beam sources which generate primary particle beams, to be precise an electron source situated in an electron-optical column and able to generate an electron beam, and an ion source situated in an ion-optical column and able to generate an ion beam.

Figure 2:
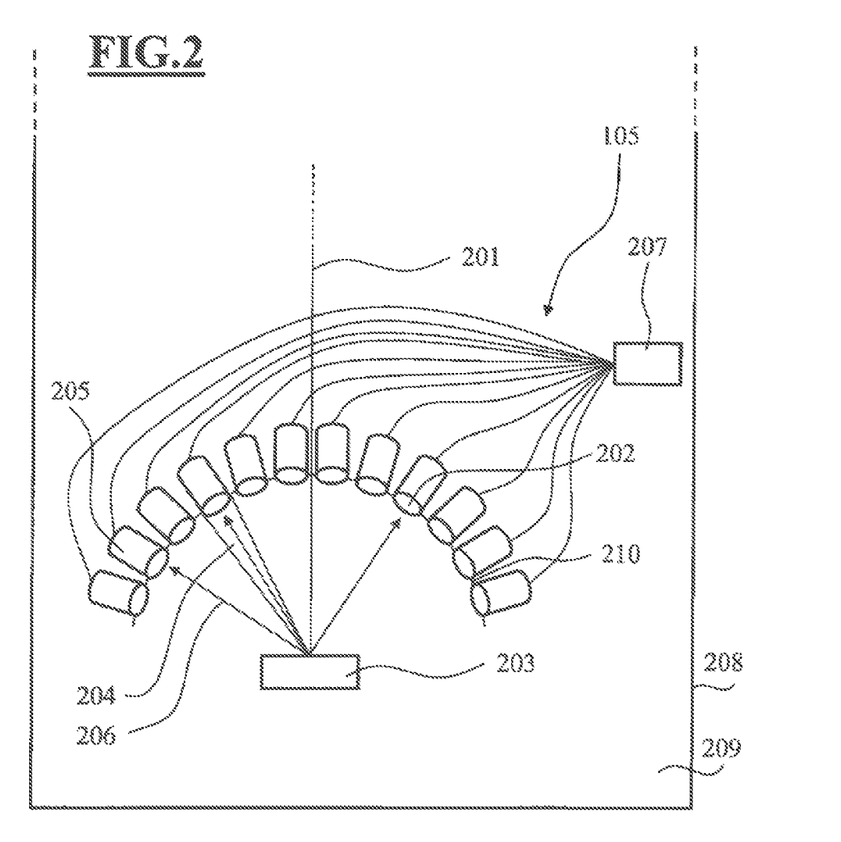
FIG. 2 schematically shows a section through an advantageous embodiment.

FIG. 2 shows an advantageous embodiment of the device according to the invention. The detection device 105 comprises a multiplicity of light-pickup elements 202 and is situated within an evacuated sample chamber 209, which is delimited by a wall 208. The light-pickup elements 202 are arranged over the sample 203 and are embodied as collecting optical units. Here, a collecting optical unit can be embodied as free-beam optical unit or as fiber-optical unit. It was found to be particularly advantageous if the light-pickup elements 202 are arranged in such a way that they form a hemispherical surface over the surface of the sample 203. Stated differently: the light-pickup elements 202 are—as depicted in a section in FIG. 2—arranged on a segment of a spherical surface. It is particularly advantageous if the intermediate surfaces 210 between the light-pickup elements 202, lying on the segment of the spherical surface, are configured from light-absorbing material such that stray-light effects are avoided. An opening situated in the continuation of the optical axis 104, 201 of the particle-optical device 101 is preferably cut out in or near the center of the segment of the spherical surface. The primary particle beam 201 is directed to the sample surface 203 through this opening. Depending on the geometric form and/or emission property of the sample, it is also feasible for the light-pickup elements 202 not to form a hemispherical surface but rather to be arranged in a different shape spanning over the sample.

It was found to be advantageous if the device overall comprises two or more light-pickup elements. It is particularly advantageous if the device comprises seven light-pickup elements such that seven solid-angle ranges can be registered accordingly. It is also feasible for the device to comprise ten or more than ten, e.g. 100, light-pickup elements. However, it should be noted in the process that although, on the one hand, the solid-angle resolution is improved with increasing number of light-pickup elements, on the other hand, the radiation portion incident on the individual light-pickup element is reduced, and so the sensitivity of the measurement arrangement is reduced. Therefore, the number of light-pickup elements should be selected in such a way that, depending on the type of application, a compromise is found between achievable angular resolution and desired sensitivity. Photons released by the sample material 203 are registered by the collecting optical units 202. Here, each collecting optical unit 202 registers the photons emitted in the associated solid-angle range 204. Thus, this means that each collecting optical unit 202 captures photons moving along trajectories 206 corresponding to a solid-angle range 204. Each of the light-pickup elements 202 embodied as collecting optical unit is connected to a miniature spectrometer 205, and so the photons captured in each case with a collecting optical unit 202 are forwarded to an assigned miniature spectrometer 205. By way of example, such miniaturized spectrometers 205 are known from DE 10304312. The spatial requirements of a miniature spectrometer 205 can typically be less than 125 mm$^3$. Due to the small dimensions thereof, the miniature spectrometers 205 can be placed in the vicinity of the measurement point, i.e. at the location at which the primary particle beam is incident on the sample and triggers the light emission, and so these, firstly, are able to register a large solid angle and, secondly, do not shadow further detectors which detect e.g. secondary electrons or back-scattered electrons. The integration times of the miniature spectrometers 205 are usually a few milliseconds. The miniature spectrometers 205 can be embodied as single-channel spectrometers or as multi-channel spectrometers, for example with two, three or more channels.

The miniature spectrometers 205 generate spectra of the respectively detected luminescence light. The obtained spectra are forwarded to an analysis system 207, stored and evaluated. In an alternative configuration of this embodiment, the generated spectra are stored and evaluated in miniature spectrometers 205.

What is common to both configurations is that the obtained spectra can respectively be assigned to a specific solid-angle range of the respective photon trajectories. Therefore, it is thus possible to detect the luminescence light in an angle-resolved manner and to analyze it spectrally. The obtained spectra can then be calculated by mathematical algorithms on the basis of chemical statistics (chemometrics) and be analyzed and evaluated with the aid of available databases.

Since the luminescence light is respectively only emitted at the point of incidence of the primary particle beam, a spatial resolution of the luminescence signal can moreover be achieved if the focus of the primary particle beam is guided, perpendicular to the optical axis thereof, over the sample surface in a time-sequential manner and the respective angle-resolved and spectrally resolved signal is assigned to that point on the sample on which the primary particle beam is incident at the respective time.

Figure 3:
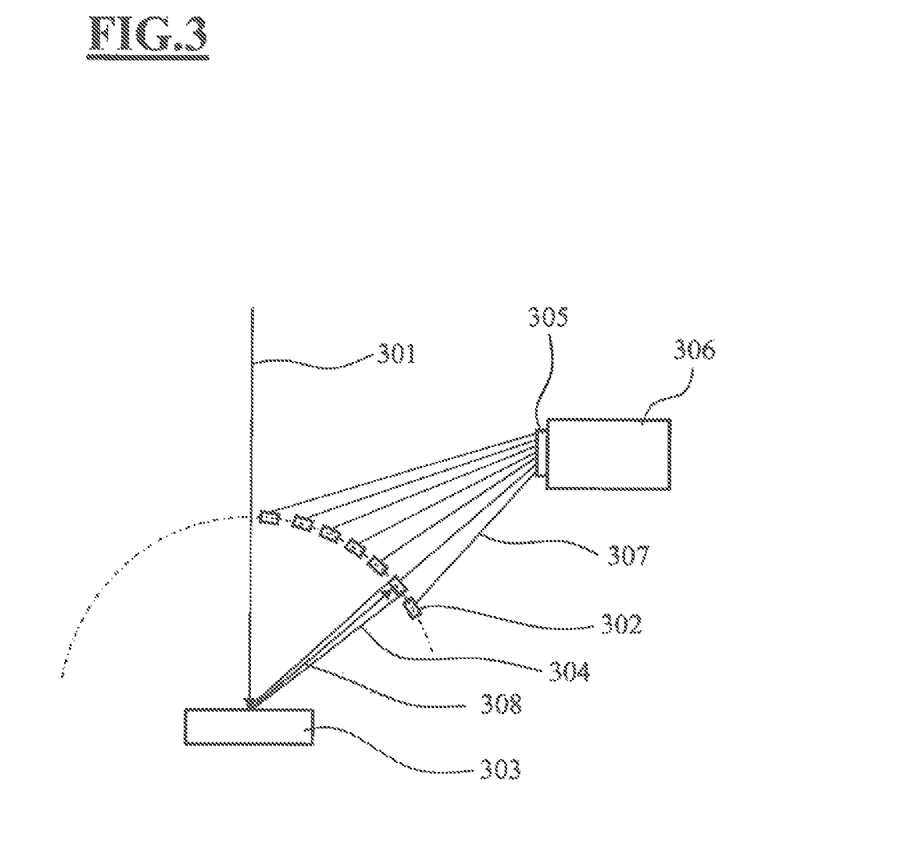
FIG. 3 schematically shows a section through a further advantageous embodiment.

In a further advantageous embodiment, which is depicted in FIG. 3, the light-pickup elements 302 are embodied as light-entry openings of optical fibers 307. The optical fibers 307 can have a diameter between 50 μm and 800 μm, preferably between 80 μm and 100 μm. It is also feasible for the optical fibers 307 to have a diameter of less than 50 μm or more than 800 μm. The light-entry openings 302 are arranged on the side of the optical fibers 307 facing the sample 303. Each light-entry opening 302 collects light which was emitted in a solid-angle range 304 of the trajectories 308. Photons which were picked up by the light-entry openings 302 are forwarded via the optical fibers 307 to the entry slit 305 of a multi-channel spectrometer 306. The multi-channel spectrometer 306 can preferably comprise an integrated evaluation unit. By way of example, the multi-channel spectrometer 306 can be embodied as an Offner spectrometer with e.g. 30 channels such that 30 spectra can be recorded simultaneously. It was also found to be advantageous in this embodiment if the light-entry openings 302 are arranged on the surface of the spherical segment. Thus, this means that the multiplicity of light-entry openings 302 in their ttality form the shape of a segment of a spherical surface. The individual light-entry openings 302 comprise collecting optical units or free-beam optical units. If the focus of the primary particle beam 301—as described in relation to FIG. 2—is guided time sequentially over the sample surface, it is also possible to record spectra with a spatial and/or angular resolution using this embodiment.

Furthermore, a time-resolving photon detector, e.g. a PMD chip can be used in the employed multi-channel spectrometer 306 for recording spectra. A photonic mixer device (abbreviated: PMD) chip is an optoelectronic detector which registers both amplitude and phase (i.e. the time profile) of a received light pulse or of time-modulated light. By modulating the excitation energy, for example by switching the primary particle beam off and on, or by changing the acceleration voltage (and hence the mean energy of the primary particles), it is possible to register and detect time-varying spectral properties of the emitted photons. Therefore, this means that the released luminescence light can be detected in a time-resolved manner, with a time resolution of 1 ns being possible. The time-resolving photon detector may e.g. be embodied in the form of a matrix sensor or a line sensor or a point sensor. Alternatively, it is feasible to achieve the time resolution by virtue of e.g. the excitation being provided in the form of a short pulse and the resultant luminescent response being detected in a time-dependent manner. Another option lies in registering the emitted luminescence signal in a time-resolved manner with the aid of a spectrometric measurement arrangement, which comprises a fast shutter on the entry slit.

A further advantageous embodiment comprises a first spectrometer, which uses the radiation portion undergoing higher-order diffraction, that is to say e.g. first, second or third order, for the detection, and also a second spectrometer, which uses the radiation portion undergoing zero-order diffraction in the first spectrometer. By using the zero-order radiation, the second spectrometer can be operated at the same time as the first spectrometer, without the first spectrometer losing performance in the process. This is possible because the amount of light incident on the first spectrometer is not reduced and therefore the function of the first spectrometer is not impaired by the operation of the second spectrometer. It was found to be advantageous if the first spectrometer e.g. registers a wavelength range from 350 nm-1700 nm, while the second spectrometer registers a narrower wavelength range, e.g. 360 nm-780 nm, and operates at a higher resolution than the first spectrometer. However, the invention is not restricted to this exemplary embodiment since the properties of the first and of the second spectrometer can be selected depending on the problem posed. Thus, it is for example also feasible for adjacent wavelength ranges to be registered by the first and second spectrometer by virtue of the first spectrometer registering a first wavelength range and the second spectrometer registering a second wavelength range, wherein the first and second wavelength range differ from one another and adjoin one another or do not adjoin one another.

In contrast to conventional spectrometers, in which the spectrometric measurement needs to be interrupted for referencing, it is moreover possible to reference the spectra simultaneously and in parallel. This is brought about by virtue of a plurality of channels being used, and so separate channels can be used for referencing. This can be brought about by virtue of the light beam being split losslessly or approximately losslessly—for example via a dichroic mirror—such that part of the light is fed to the spectrometric measurement while another part of the light serves for carrying out the referencing. This can be brought about by virtue of minimum and maximum value of the measurement arrangement being set with the aid of an external standard, the luminescence property of which is known. Alternatively, the sample itself can be employed as internal reference standard. To this end, luminescence signals, which are emitted by the sample but are not object of the actual analysis, are used to set the measurement arrangement for the examination and/or to compensate for undesired system changes.

Figure 4:
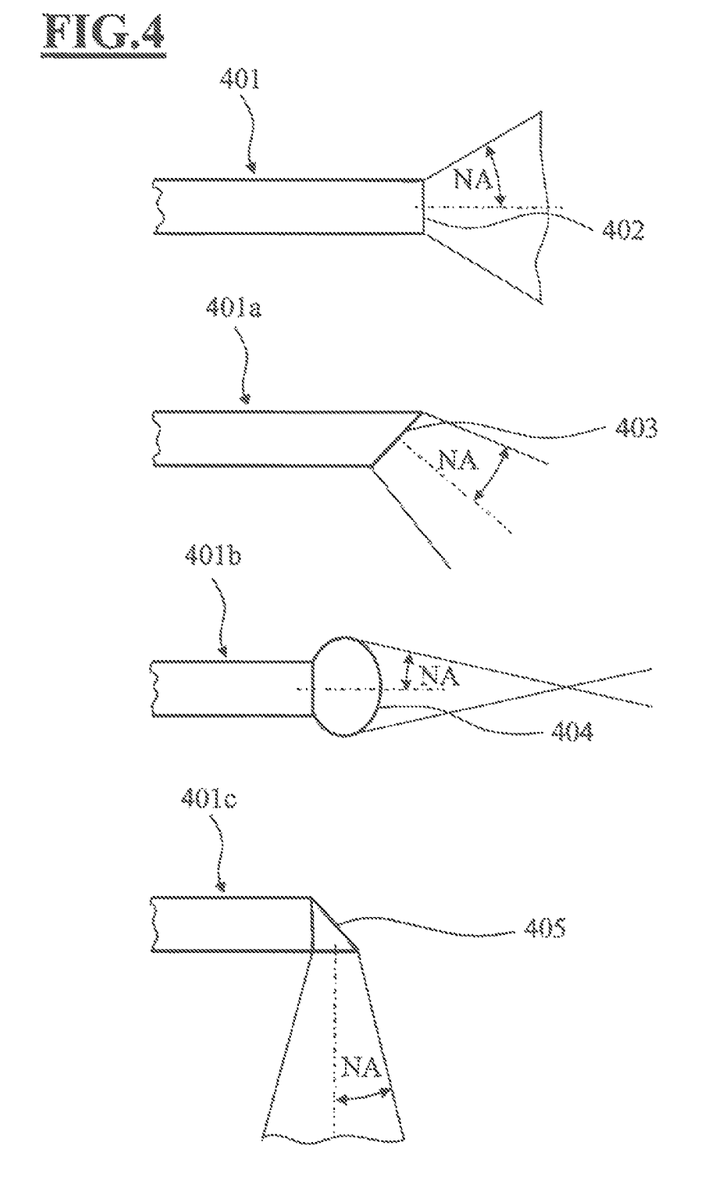
FIG. 4 schematically shows a section through advantageous embodiments of the light-entry openings.

As depicted in FIG. 4, the light-entry openings 402, 403, 404, 405 of the optical fibers 401, 401a, 401b, 401c can have different embodiments, for example as a polished fiber end face 402, as an angled polished fiber end face 403, as a spherical optical unit 404 or as a prism 405. In the simplest case—the polished fiber end face 402—the fiber end is embodied with a straight cut with a polish. Alternatively, the fiber end can be cut-off at an angle and polished such that an angled polished fiber end face 403 was generated. Advantageously, the angle should be selected depending on the utilized material in such a way that no adverse effects, such as e.g. total internal reflection, occur. A spherical optical unit 404 is understood to mean that the fiber end is embodied as a spherical or hemispherical lens element, or else with an aspherical optical unit. In the case of the prism 405, the fiber end is embodied as a prism optical unit. The various embodiments 402, 403, 404, 405 differ in terms of achievable numerical aperture (NA), which may typically lie between 0.22 and 0.44.

It was found to be advantageous for the various embodiments of the light-entry openings to be combined in a detection device. Here, the embodiment of each individual light-entry opening should be selected, depending on the point on the spherical surface segment on which this light-entry opening is situated, in such a way that the totality of light-entry openings capture the light emitted by the sample material as efficiently as possible.

In a particularly advantageous embodiment, the light-entry openings are antiglare—independent of the respective configuration. By way of example, the antiglare property can be achieved by the application of a microstructured surface or suitable coating.

An additional metalization of the surfaces of the optical fibers by vapor deposition or sputtering of e.g. aluminum or gold has the advantageous effect that the optical fibers become electrically conductive, and so this can prevent undesired electric charging of the components during the operation of the particle-optical device. Alternatively, the electric conductivity of the optical fibers can be brought about by coating with indium tin oxide (ITO) such that a conductive surface coating is obtained, which is moreover transparent.

Figure 5A:
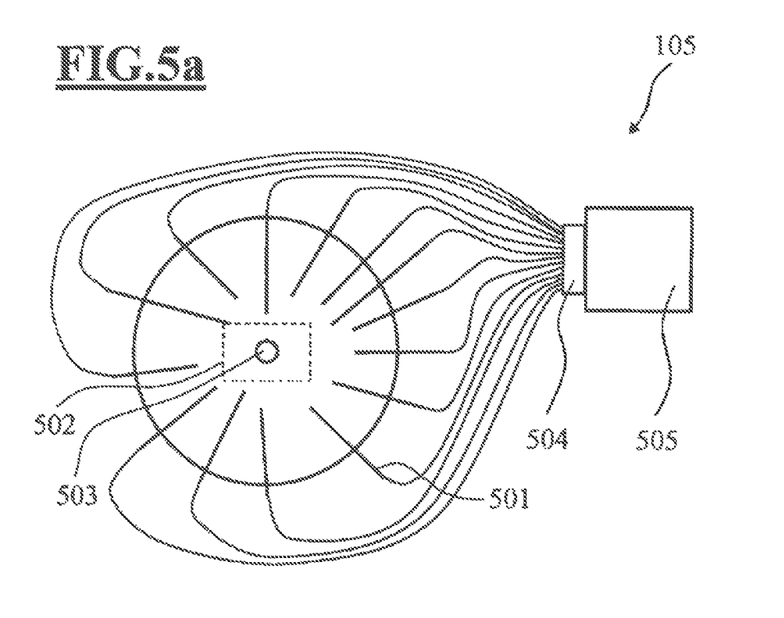
FIG. 5a shows a top view.
Figure 5B:
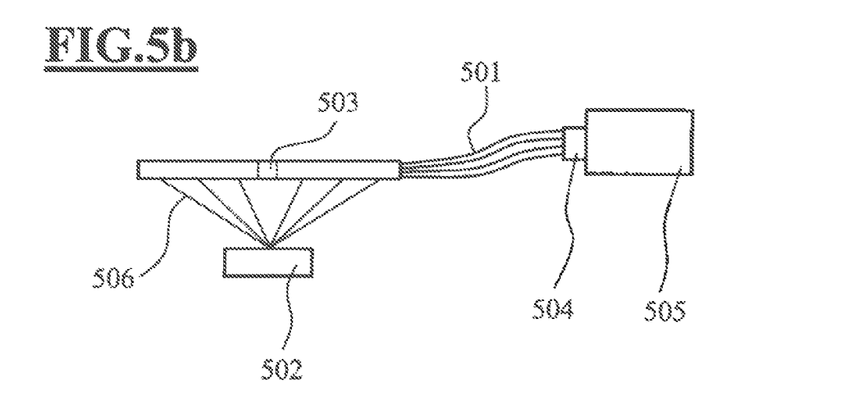
FIG. 5b shows a sectional view.

A further advantageous embodiment is depicted in FIG. 5a (top view) and FIG. 5b (sectional view). In this embodiment, the various embodiments of the light-entry openings depicted in FIG. 4 are combined in such a way that a planar structure is generated, via which an angle-resolved detection is possible. Here, the light-pickup elements are arranged in such a way that the totality of light-entry openings of the many light-pickup elements are arranged in a plane. An advantage thereof is that the detection device 105 can be installed in the particle-optical device 101 in a space-saving manner, for example between sample 103, 502 and particle-optical column 106. In the planar embodiment, an opening 503 is cut-out—preferably in or near the center of the planar structure—in which the continuation of the optical axis 104 of the particle-optical device 101 is situated. The primary particle beam is directed to the surface of the sample 502 through this opening 503. Via optical fibers 501, the photons picked up by the light-entry openings are, as already described in the exemplary embodiment in FIG. 3, guided to the entry slit 504 of a multi-channel spectrometer 505, which may comprise an evaluation unit, and analyzed there.

Figure 6:
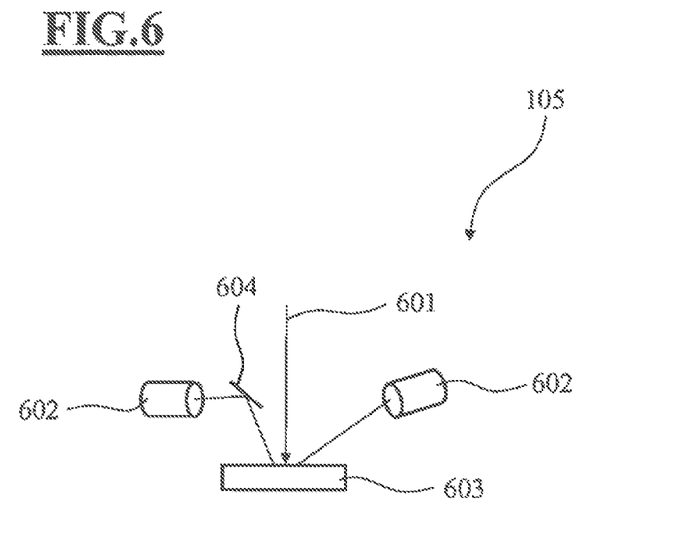
FIG. 6 schematically shows the sectional view of a further advantageous embodiment.

FIG. 6 depicts a further advantageous embodiment of the invention in the sectional view. In this embodiment, the detection device 105 comprises a multiplicity of light-pickup elements 602, of which two light-pickup elements 602 are depicted in an exemplary manner. The light-pickup elements 602 are embodied as collecting optical units and connected to miniature spectrometers. The collecting optical units of the miniature spectrometers 602 are arranged in a plane above the sample 603. By using mirrors 604 and employing the Scheimpflug effect, it is possible via this planar arrangement of light-pickup elements 602 and miniature spectrometers to detect, in an angle-resolved manner, photons emitted when the primary particle beam 601 is incident on the sample 603. The detection device comprises mirrors 604, which are arranged in such a way that photons are deflected in such a way that they are incident on a collecting optical unit and are detected. In order to employ the Scheimpflug effect, the main plane of the collecting optical unit of the respective miniature spectrometer and the image plane of the miniature spectrometer are tilted at a specific angle with respect to one another such that the sample plane, main plane of the collecting optical unit and image plane of the miniature spectrometer intersect along a common straight line. If this condition is satisfied, the sample 603 can be imaged in focus over large regions, even if the sample plane is at an angle in relation to the image plane of the miniature spectrometer. In this embodiment too, it is particularly advantageous that the detection device can be installed in the particle-optical device 101 in a space-saving manner, for example between particle-optical column 106 and sample 603.

Figure 7:
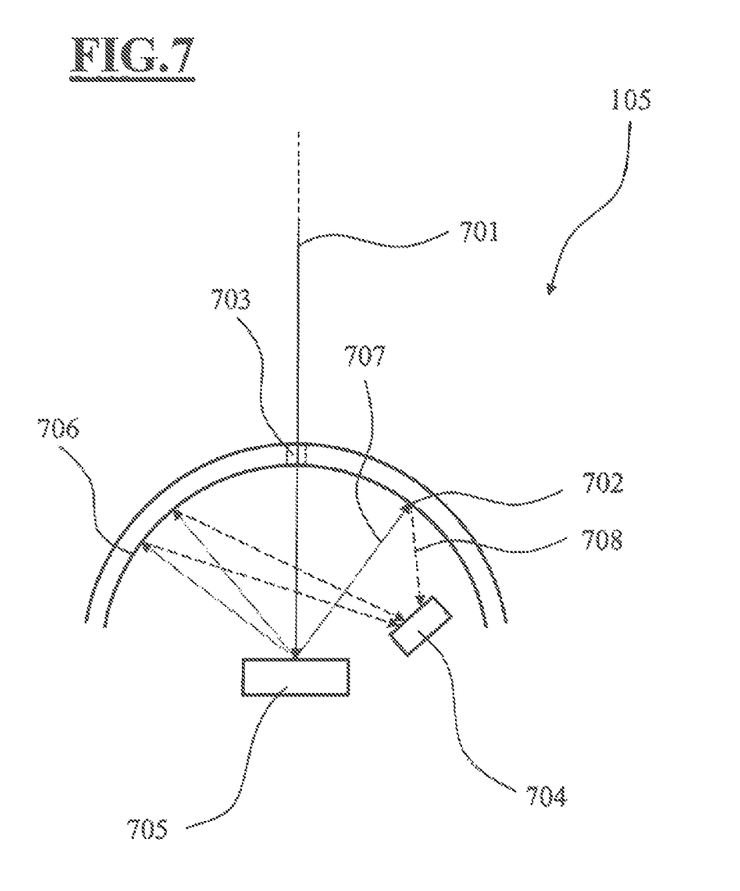
FIG. 7 schematically shows a section through a further advantageous embodiment.

FIG. 7 depicts a further exemplary embodiment, in which the number of elements in the beam path is minimized such that the luminescence light can be used particularly efficiently. The detection device 105 comprises an imaging grating 702 and a detector 704. The imaging grating 702 can be embodied as a concave hemispherical surface. Advantageously, the hemispherical surface has an opening 703, which can be penetrated by the primary particle beam 701 in order then to be incident on the sample 705 lying under the imaging grating 702. In an alternative embodiment, the imaging grating 702 is merely embodied as a segment 706 of the hemispherical surface. In both embodiments, the imaging grating 702 is arranged in such a way that photons released by the sample 705 are dispersed such that a spectrum is generated. The generated spectrum is detected and stored by detector 704. The components of the detection device 105 are therefore arranged and designed in such a way that luminescence light is emitted in all spatial directions when a primary particle beam 701 is incident on the sample 705. Here, a first partial beam 707 of the luminescence light is reflected at the grating 702 and directed in the form of a second partial beam 708 in the direction of the detector 704 such that the second partial beam 708 is incident on the detector surface 704. Here, partial beams 707, which were emitted in different solid-angle ranges by the sample 705, are incident on the detector surface 704 at different points and are detected there. On the other hand, partial beams 707 emitted by the sample 705 are dispersed on the grating such that they—split into the wavelengths thereof—are incident on the detector surface 704 and analyzed spectrally. This is brought about independently of the point of incidence on the sample 705. The detector 704 can be embodied as a line detector or as a matrix detector, wherein the use of a matrix detector enables a spatial resolution. As a result of the spatial resolution of the matrix detector 704, it is therefore possible, in an angle-resolved manner, to detect and register the luminescence light emerging from the sample 705 since luminescence light emitted into different solid-angle ranges is deflected to different points of the matrix detector 704 by the grating 702.

It is a characteristic of this exemplary embodiment that the number of elements in the beam path has been minimized since the light-emitting point on the sample 705 simultaneously constitutes the entry slit of a spectrometric measurement arrangement. The spectrometric measurement arrangement comprises the sample (as entry slit) 705, the imaging grating 702 and the detector 704. In this manner, the luminescence light can be employed with the greatest possible efficiency.

As an alternative to the above-described particularly advantageous spherical embodiment, the imaging grating 702 can have an aspherical embodiment. It was moreover found to be advantageous if the imaging grating 702 was produced holographically, independently of the form of the embodiment.

Figure 8:
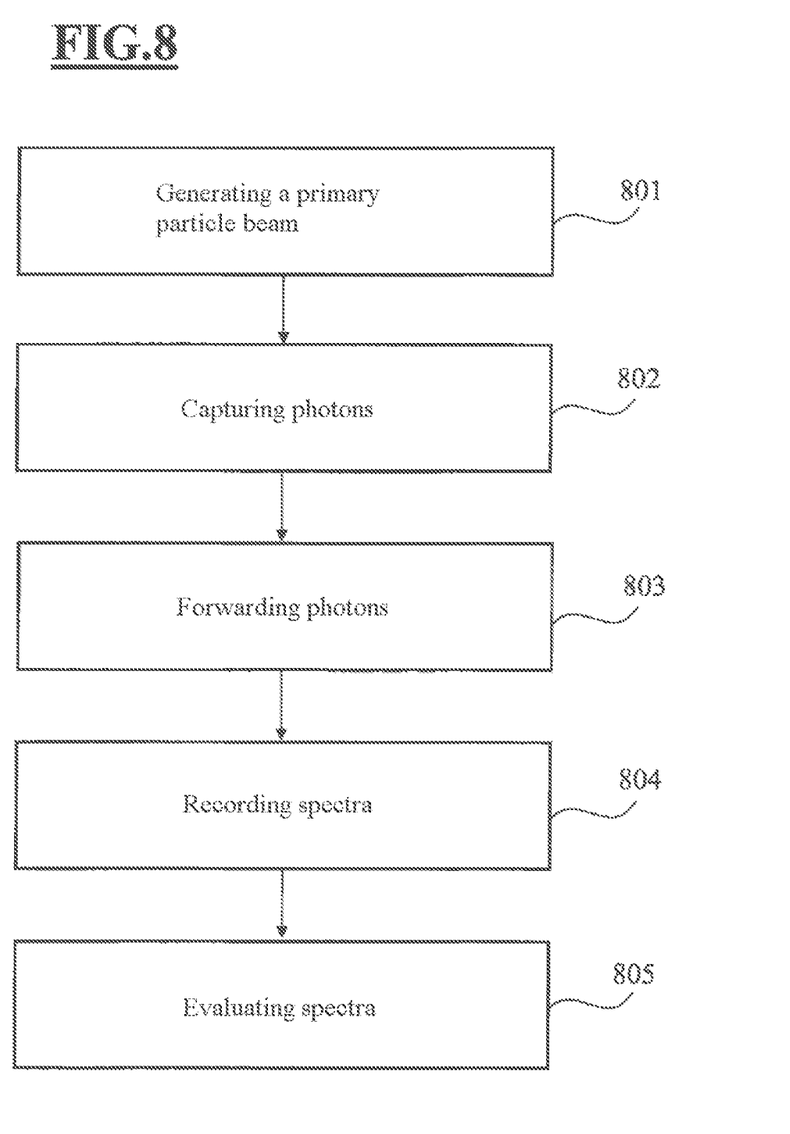
FIG. 8 shows a flowchart of a method according to the invention.

FIG. 8 shows the flow chart of a method according to the invention for spectroscopic analysis of samples. A primary particle beam directed to the sample is generated in a first step 801. The primary particle beam can be an electron beam and/or an ion beam. The primary particle beam is incident on the sample and releases photons from the sample due to the interaction between primary particle beam and sample material. The released photons can move along a multiplicity of possible trajectories, wherein each one of the possible trajectories n is characterized by an elevation angle $h_n$ and an azimuth angle $a_n$, and equal or similar trajectories are combined to form solid-angle ranges of the trajectories. In the next step 802, the released photons are captured simultaneously by a multiplicity of light-pickup elements, wherein each individual light-pickup element registers a solid-angle range of the trajectories. In the next step 803, the captured photons are forwarded to an analysis system. The analysis system comprises a multiplicity of evaluation units, and so an evaluation unit is assigned to each light-pickup element. The analysis system can comprise a multi-channel spectrometer, i.e. a spectrometer with which a plurality of complete spectra can be recorded simultaneously, or a multiplicity of miniaturized spectrometers. In step 804, optical spectra are recorded in such a way that a spectrum is generated for each light-pickup element on the basis of the photons captured by this light-pickup element. Therefore, this means that each recorded spectrum corresponds to a solid-angle range of the trajectories. Thus, cathodoluminescence is detected separately over a multiplicity of different solid-angle ranges, wherein a multiplicity can advantageously be ten or more solid-angle ranges. In a subsequent optional step 805, the recorded optical spectra are evaluated. This is preferably brought about in a computer-assisted manner since large amounts of data have to be processed. It is advantageous if comparison spectra are already available and stored in a database, to which comparison spectra the newly obtained spectra can be compared. It is moreover feasible for this data collection to be complemented and extended by the newly obtained and evaluated spectra such that the device used for the method can be calibrated by the user for a specific application.

Since the spectra can be obtained in an angle-resolved and/or time-resolved and/or spatially resolved manner, it is sensible to evaluate the spectra using chemometric processes suitable for multidimensional data. Here, the angular resolution provides information about material properties and texture of the sample, also from different sample depths. The time resolution supplies information about the kinetics of the luminescence reaction, which in turn allows conclusions to be drawn about the material properties of the sample material. Since the emission of luminescence light is influenced by the surface topography of the sample, it is possible to draw conclusions about the sample topography.

The processes applied during the evaluation are dependent on the respective sample and the respective question. The multidimensionality of the data requires a computer-assisted evaluation, with different processes being known, e.g. those described in Naes T. et al. (2002): "A User-Friendly Guide to Multivariate Calibration and Classification", NIR Publications, Chichester, UK and in Marini, F. et al.: "Artificial Neural Networks in Chemometrics: History, Examples and Perspectives, Multivariate Analysis and Chemometrics applied to Environmental and Cultural Heritage", Nemi (RM), 2-4 Oct. 2006, Italy, such as, for example, multivariate statistical methods, discriminant and cluster analysis, multiple linear regression, principal component regression, principal component analysis, multivariate curve analysis, wavelet transform, genetic algorithms, neural networks or support vector machines. Here, the evaluation is carried out in such a way that the obtained results can be represented in a user-friendly manner.

All embodiments described previously are not restricted to the detection of photons generated by cathodoluminescence. It is also possible to detect light emitted as a result of other excitation processes, e.g. as a result of photoluminescence, electroluminescence, chemoluminescence or bioluminescence. Moreover, it is feasible to trigger luminescence phenomena with the aid of a focused ion beam and to detect these in accordance with the invention. By way of example, such a focused ion beam can be generated via a gallium ion source, wherein the emitted gallium ions are accelerated and focused with the aid of suitable lens-element systems such that they are incident on the sample surface as a focused ion beam. Alternatively, use can also be made of other ion sources, for example a helium gas field ion source.

LIST OF REFERENCE SIGNS

101 Particle-optical device
102 Sample chamber
103 Sample
104 Optical axis
105 Detection device
106 Particle-optical column
107 Analysis system
108 Detector
109 Particle beam source
110 Lens-element system
111 Lens-element system
112 Aperture stop
113 Deflection system
201 Primary particle beam
202 Light-pickup element with collecting optical unit
203 Sample
204 Solid-angle range of a trajectory
205 Miniature spectrometer
206 Trajectory
207 Analysis system
208 Wall of the sample chamber
209 Sample chamber
210 Intermediate surface
301 Primary particle beam
302 Light-pickup element with light-entry opening
303 Sample
304 Solid-angle range of a trajectory
305 Entry slit
306 Multi-channel spectrometer
307 Optical fiber
308 Trajectory
401 Optical fiber
401a Optical fiber
401b Optical fiber
401c Optical fiber
402 Fiber end face
403 Angled fiber end face
404 Fiber end with a spherical optical unit
405 Fiber end with a prism
NA Numerical aperture
501 Optical fiber
502 Sample
503 Opening
504 Entry slit
505 Multi-channel spectrometer
506 Trajectory
601 Primary particle beam
602 Miniature spectrometer
603 Sample
604 Mirror
701 Primary particle beam
702 Imaging grating
703 Opening
704 Detector
705 Sample
706 Hemispherical segment
707 First partial beam
708 Second partial beam
801 Step: generating a primary particle beam
802 Step: capturing photons
803 Step: forwarding photons
804 Step: recording spectra
805 Step: evaluating spectra

The invention claimed is:

1. A device, comprising:
   an imaging grating configured to disperse photons released by a sample; and
   a detector configured to detect the spectrum generated by the dispersion of the photons.

2. The device of claim 1, wherein the detector comprises a detector selected from the group consisting of a line detector and a matrix detector.

3. The device of claim 1, wherein the imaging grating comprises a hemispherical surface.

4. The device of claim 1, wherein the imaging grating comprises a segment of a hemispherical surface.

5. The device of claim 1, wherein the imaging grating comprises an aspherical imaging grating.

6. The device of claim 1, wherein the imaging grating comprises a holographic imaging grating.

7. A device, comprising:
   a particle beam source configured to generate a primary particle beam directable to a sample so that, when the primary particle beam is incident on the sample, photons are released from the sample due to the interaction between primary particle beam and the sample;
   an imaging grating configured to disperse the photons released by the sample; and
   a detector configured to detect the spectrum generated by the dispersion of the photons.

8. The device of claim 7, wherein the detector comprises a detector selected from the group consisting of a line detector and a matrix detector.

9. The device of claim 7, wherein the imaging grating comprises a hemispherical surface.

10. The device of claim 7, wherein the imaging grating comprises a segment of a hemispherical surface.

11. The device of claim 7, wherein the imaging grating comprises an opening configured to allow passage of the primary particle beam.

12. The device of claim 7, wherein the imaging grating comprises an aspherical imaging grating.

13. The device of claim 7, wherein the imaging grating comprises a holographic imaging grating.

14. The device of claim 7, wherein the device is configured so that photons emitted from the sample at different solid angles are incident on the detector at different locations.

15. A method, comprising:
  directing a primary particle beam to a sample so that the primary particle beam is incident on the sample and photons are released from the sample due to the interaction between the primary particle beam and the sample and so that released photons move along a multiplicity of possible trajectories, wherein each one of the possible trajectories is characterized by an elevation angle and an azimuth angle, and equivalent or similar trajectories are combined to solid-angle ranges of the trajectories;
  capturing the released photons via an imaging grating that disperses the photons released by the sample; and
  detecting the spectrum generated by the dispersion of the photons.

16. The method of claim 15, further comprising evaluating the detected spectrum.

17. The method of claim 15, wherein the photons are detected in an angularly resolved manner.

18. The method of claim 15, wherein the imaging grating comprises a hemispherical surface.

19. The method of claim 15, wherein the imaging grating comprises a segment of a hemispherical surface.

20. The method of claim 15, wherein the imaging grating comprises an opening configured to allow passage of the primary particle beam.

* * * * *

UNITED STATES PATENT AND TRADEMARK OFFICE
CERTIFICATE OF CORRECTION

PATENT NO. : 10,436,712 B2
APPLICATION NO. : 15/909008
DATED : October 8, 2019
INVENTOR(S) : Nico Correns and Michael Rode Page 1 of 1

It is certified that error appears in the above-identified patent and that said Letters Patent is hereby corrected as shown below:

In the Specification

Column 8, Line 57, delete "ttality" and insert -- totality --, therefor.

Signed and Sealed this
Fourteenth Day of April, 2020

Andrei Iancu
*Director of the United States Patent and Trademark Office*